US009181275B2

(12) United States Patent
Cowart et al.

(10) Patent No.: US 9,181,275 B2
(45) Date of Patent: Nov. 10, 2015

(54) MERCAPTOAMIDINE DERIVATIVES AND METHODS OF USE

(75) Inventors: Marlon D. Cowart, Round Lake Beach, IL (US); Huaqing Liu, Buffalo Grove, IL (US); Robert Altenbach, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 256 days.

(21) Appl. No.: 13/571,070

(22) Filed: Aug. 9, 2012

(65) Prior Publication Data

US 2013/0040940 A1 Feb. 14, 2013

Related U.S. Application Data

(60) Provisional application No. 61/522,656, filed on Aug. 11, 2011.

(51) Int. Cl.
*A61K 31/551* (2006.01)
*C07D 513/04* (2006.01)

(52) U.S. Cl.
CPC .................... *C07D 513/04* (2013.01)

(58) Field of Classification Search
CPC ............................ C07D 513/04; A61K 31/551
USPC ........................................... 514/220; 540/560
See application file for complete search history.

(56) References Cited

FOREIGN PATENT DOCUMENTS

| WO | WO-2004043458 A1 | 5/2004 |
| WO | WO-2006103537 A2 | 10/2006 |
| WO | WO-2006103546 A2 | 10/2006 |

OTHER PUBLICATIONS

Airaksinen M.S., et al., "Histamine Neurons in Human Hypothalamus: Anatomy in Normal and Alzheimer Diseased Brains," Neuroscience, 1991, vol. 44 (2), pp. 465-481.
Arrang J.M., et al., "Auto-inhibition of Brain Histamine Release Mediated by a Novel Class (H.sub.3) of Histamine Receptor," Nature, 1983, vol. 302, pp. 832-837.
Arrang J.M., et al., "Highly Potent and Selective Ligands for Histamine H.sub.3-Receptors," Nature, 1987, vol. 327, pp. 117-123.
Arrang J.M., et al., "Histamine H.sub.3 Receptor Binding Sites in Rat Brain Membranes:Modulations by Guanine Nucleotides and Divalent Cations," European Journal of Pharmacology, 1990, vol. 188, pp. 219-227.
Barbier A.J., et al., "Acute Wake-Promoting Actions of JNJ-5207852, a Novel, Diamine-based H.sub.3 Antagonist," British Journal of Pharmacology, 2004, vol. 143, pp. 649-661.
Bernaerts P., et al., "Histamine H3 Antagonist Thioperamide Dose-Dependently Enhances Memory Consolidation and Reverse Amnesia Induced by Dizocilpine or Scopolamine in a One-Trail Inhibitory Avoidance Task in Mice," Behavioural Brain Research, 2004, vol. 154, pp. 211-219.
Bjenning, C. et al., "Peripherally administered Ciproxifan elevates hypothalamic histamine levels and potently reduces food intake in the Sprague Dawley rat," Histamine Research in the New Millenium (2001) 449-451; Abstracts, International Sendai Histamine Symposium, Sendai, Japan, #P39, Nov. 2000.
Browman K.E. et al., "Enhancement of Prepulse Inhibition of Startle in Mice by the H3 Receptor Antagonists Thioperamide and Ciproxifan," Behavioural Brain Research, 2004, vol. 153 (1), pp. 69-76.
Chaplan S.R., et al., "Quantitative Assessment of Tactile Allodynia in the Rat Paw," Journal of Neuroscience Methods, 1994, vol. 53 (1), pp. 55-63.
Chen Z., et al., "Effects of Histamine on MK-801-induced Memory Deficits in Radial Maze Performance in Rats," Brain Research, 1999, vol. 839, pp. 186-189.
Chen Z., et al., "Pharmacological Effects of Carcinine on Histaminergic Neurons in the Brain," British Journal of Pharmacology, 2004, vol. 143, pp. 573-580.
Cheng Y., et al., "Relationship Between the Inhibition Constant (KI) and the Concentration of Inhibitor Which Causes 50 Per Cent Inhibition (I.sub.50) of An Enzymatic Reaction ," Biochemical Pharmacology, 1973, vol. 22 , pp. 3099-3108.
Clapham J., et al., "Thioperamide, the Selective Histamine H3 Receptor Antagonist, Attenuates Stimulant Induced Locomotor Activity in the Mouse," European Journal of Pharmacology, 1994, vol. 259 (2), pp. 107-114.
Cowart M., et al., "4-(2-[2-(2(R)-Methylpyrrolidin-1-yl) ethyl] Benzofuran-5yl) Benzonitrile and Related 2-Aminoethylbenzofuran H3 Receptor Antagonists Potently Enhance Cognition and Attention," Journal of Medicinal Chemistry , 2005, vol. 48 (1), pp. 38-55.
De Almeida M.A., et al., "Memory Facilitation by Histamine," Archives Internationales De Physiologie Et De Biochimie, 1986, vol. 283 (2), pp. 193-198.
Delaunois A., et al., "Modulation of Acetylcholine, Capsaicin and subsztance P Effects by Histamine H.sub.3 Receptors in Isolated Perfused Rabbit Lungs," European Journal of Pharmacology, 1995, vol. 277 (2-3), pp. 243-250.
Dimitriadou V., et al., "Functional Relationship Between Mast Cells and C-Sensitive Nerve Fibres Evidenced by Histamine H.Sub.3-Receptor Modulation in Rat Lung and Spleen," Clinical Science, 1994, vol. 87, pp. 151-163.
Dixon W.J., "Efficient Analysis of Experimental Observations," Annual Review of Pharmacology and Toxicology, 1980, vol. 20, pp. 441-462.
Dumery V., et al., "Development of Amygdaloid Cholinergic Mediation of Passive Avoidance Learning in the Rat," Experimental Brain Research , 1987, vol. 67(1), pp. 61-69.

(Continued)

*Primary Examiner* — Brenda Coleman
(74) *Attorney, Agent, or Firm* — Lisa V. Mueller; Michael Best & Friedrich LLP

(57) ABSTRACT

Compounds of formula (I)

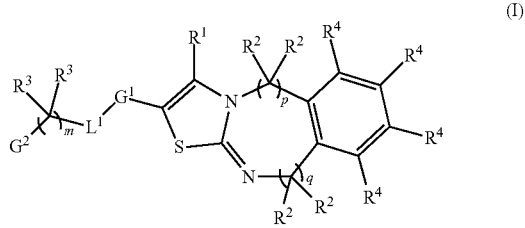

are useful in treating conditions or disorders prevented by or ameliorated by histamine-3 receptor ligands. Also disclosed are pharmaceutical compositions of compounds of formula (I), methods for using such compounds and compositions, and a process for preparing the compounds.

11 Claims, No Drawings

(56) References Cited

OTHER PUBLICATIONS

Dvorak C.A., et al., "4-Phenoxypiperidines: Potent, Conformationally Restricted, non-Imidazole Histamine H3 Antagonists," Journal of Medicinal Chemistry, 2005, vol. 48 (6), pp. 2229-2238.

Elslager E. F., et al., "The synthesis of 5,10-dihydro- and 2,3,5,10-tetrahydrothiazolo-[3,2-b][2,4] benzodiazepines, 1,2,3,4,7,12-hexahydrobenzothiazolo-[3,2-b][2,4]benzodiazepine, and 9-14-dihydro-6H-[1]benzothiopyrano-[4',3':4,5]thiazolo[3,2-b][2,4]benzodiazepine via 1,2,4,5-tetrahydro-3H-2,4-benzodiazepine-3-thione," Journal of Heterocyclic Chemistry, 1968, vol. 5, pp. 609-613.

Esbenshade T.A., et al., "Pharmacological and Behavioral Properties of A-349821, a Selective and Potent Human Histamine H3 Receptor Antagonist," Biochemical Pharmacology, 2004, vol. 68 (5), pp. 933-945.

Esbenshade T.A., et al., "Pharmacological Properties of ABT-239 [4-(2-{2-[(2R)-2-Methylpyrrolidinyl]ethyl}-benzofuran-5-yObenzonitrile]: I. Potent and Selective Histamine H3 Receptor Antagonist with Drug-Like Properties," Journal of Pharmacology and Experimental Therapeutics, 2005, vol. 313 (1), pp. 165-175

Fitzsimons C., et al., "Histamine Receptors Signaling in Epidermal Tumor Cell Lines with H-Ras Gene Alterations," Inflammation Research, 1998, vol. 47 (1), pp. S50-S51.

Fox G.B, et al., "Effects of Histamine H3 Receptor Ligands GT2331 and Ciproxifan in a Repeated Acquisition Response in the Spontaneously Hypertensive Rat Pup," Behavioural Brain Research, 2002, vol. 131 (1-2), pp. 151-161.

Fox G.B., et al., "Identification of Novel H3 Receptor (H3R Antagonists with Cognition Enhancing Properties in Rats," Inflammation Research, 2003, vol. 52 (1), pp. S31-S32.

Fox G.B., et al., "Pharmacological Properties of ABT-239 [4-(2-{2-[(2R)-2-Methylpyrrolidinty]ethyl}-benzofuran-5-yl)benzonitrile]- : II Neurophysiological Characterization and Broad Preclinical Efficacy in Cognition and Schizophrenia of a Potent and Selective Histamine H3 R," Journal of Pharmacology and Experimental Therapeutics, 2005, vol. 313 (1), pp. 176-190.

Fox G.B., et al., "Two Novel and Selective Nonimidazole H3 Receptor Antagonists A-304121 and A-317920: II. In Vivo Behavioral and Neurophysiological Characterization," Journal of Pharmacology and Experimental Therapeutics, 2003, vol. 305 (3), pp. 897-908.

Furniss B.S., et al., Vogel's Textbook of Practical Organic Chemistry, 5th Edition, Longman Scientific & Technical, 1989, Table of Contents.

Gaffield W., et al., "Chiroptical Properties of N-Nitrosopyrrolidines and N-Nitrosamino Acids," Tetrahedron, 1981, vol. 37, pp. 1861-1869.

Glase S.A., et al., "Attention Deficit Hyperactivity Disorder: Pathophysiology and Design of New Treatments," Annual Reports in Medicinal Chemistry, 2002, vol. 37, pp. 11-20.

Greene T.W., et al., Protective Groups in Organic Synthesis, 4th Edition, John Wiley and Sons, Inc., 2006, Table of Contents.

Haas L., et al., "Subcortical Modulation of Synaptic Plasticity in the Hippocampus," Behavioural Brain Research, 1995, vol. 66 (1-2), pp. 41-44.

Halpern, M.T., "GT-2331," Current Opinion in Central and Peripheral Nervous System Investigational Drugs, 1999, vol. 1, pp. 524-527.

Hancock A.A., et al., "Antiobesity Effects of A-331440, a Novel Non-Imidazole Histamine H3 Receptor Antagonist," European Journal of Pharmacology, 2004, vol. 487 (1-3), pp. 183-197.

Hancock A.A., et al., "Histamine H3 Antagonists in Models of Obesity," Inflammatory Research, 2004, vol. 53 (Suppl. 1), pp. S47-S48.

Harada C., et al., "Inhibitory Effect of Iodophenpropit, a Selective Histamine H3 Antagonist, on Amygdaloid Kindled Seizures," Brain Research Bulletin, 2004, vol. 63 (2), pp. 143-146.

Hriscu A., et al., "Experimental Evaluation of the Analgesic Efficacy of Some Antihistamines as Proof of the Histaminergic Receptor Involvement in Pain," Famacia, 2001, vol. 49 (2), pp. 23-30.

Huang Y.W., et al., "Effect of the Histamine $H_3$-antagonist Clobenpropit on Spatial Memory Deficits Induced by MK-801 as Evaluated by Radial Maze in Sprague-Dawley Rats," Behavioural Brain Research, 2004, vol. 151 (1-2), pp. 287-293.

Itoh E., et al., "Thioperamide, A Histamine $H_3$ Receptor Antagonist, Powerfully Suppresses Peptide YY-Induced Food Intake in Rats," Biological Psychiatry, 1999, vol. 45 (4), pp. 475-481.

IUPAC Commission on Nomenclature of Organic Chemistry: Rules for the Nomenclature of Organic Chemistry Section E: Stereochemistry, Pure and Applied Chemistry, 1976, vol. 45, pp. 13-30.

Joshi S.K., et al., "Animal Models of Pain for Drug Discovery," Expert Opinion on Drug Discovery, 2006, vol. 1 (4), pp. 323-334.

Kamei C., et al., "Influence of Certain $H_1$-Blockers on the Step-Through Active Avoidance Response in Rats," Psychopharmacology, 1990, vol. 102 (3), pp. 312-318.

Kamei C., et al., "Participation of Histamine in the Step-Through Active Avoidance Response and Its Inhibition by $H_1$-Blockers," Japan Journal of Pharmacology, 1991, vol. 57 (4), pp. 473-482.

Kim M.J., et al., "The Efficient Resulotion of Protected Diols and Hydroxy Aldehydes by Lipases: Steric Auxiliary Approach and Synthetic Applications," Bioorganic Medical Chemical Letters, 1996, vol. 6 (1), pp. 71-76.

Kim S.H., et al., "An Experimental Model for Peripheral Neuropathy Produced by Segmental Spinal Nerve Ligation in the Rat," Pain, 1992, vol. 50 (3), pp. 355-363.

Komater V.A., et al., "H3 Receptor Blockade by Thioperamide Enhances Cognition in Rats without Inducing Locomotor Sensitization," Psychopharmacology, 2003, vol. 167 (4), pp. 363-372.

Lamberti C., et al., "Antidepressant-like Effects of Endogenous Histamine and of Two Histamine H 1 Receptor Agonists in the Mouse Forced Swim Test," British Journal of Pharmacology, 1998, vol. 123 (7), pp. 1331-1336.

Leurs R., et al., eds., "The Histamine H3 Receptor: A Target for New Drugs," vol. 30, Elsevier Science B.V., 1998, Table of Contents.

Leurs R., et al., "Histamine Homologues Discriminating between Two Functional $H_3$-Receptor Assays. Evidence for $H_3$ Receptor," Journal of Pharmacology and Experimental Therapeutics, 1996, vol. 276 (3), pp. 1009-1015.

Leurs R., et al., The Histamine H3-Receptor: A Target for Developing New Drugs, Elsevier Science, 1998, vol. 39, pp. 127-165.

Leurs R., et al., "The Medicinal Chemistry and Therapeutic Potentials of Ligands of the Histamine $H_3$ Receptor," Progress in Drug Research, 1995, vol. 45, pp. 107-165.

Ligneau X., et al., "Neurochemical and Behavioral Effects of Ciproxifan, a Potent Histamine H3-Receptor Antagonist," Journal of Pharmacology and Experimental Therapeutics, 1998, vol. 287 (2), pp. 658-666.

Lin J.S., et al., "Involvement of Histaminergic Neurons in Arousal Mechanisms Demonstrated with $H_3$-Receptor Ligands in the Cat," Brain Research, 1990, vol. 523 (2), pp. 325-330.

Lozada A.F., et al., "Plasticity of Histamine $H_3$ Receptor Expression and Binding in the Vestibular Nuclei After Labyrinthectomy in Rat," Biomedical Center Neuroscience, 2004, vol. 5, pp. 32.

Malmberg Aiello P., et al., "Role of Histamine in Rodent Antinociception," British Journal of Pharmacology, 1994, vol. 111 (4), pp. 1269-1279.

Mazurkiewicz-Kwilecki I.M., et al., "Changes in the Regional Brain Histamine and Histidine Levels in Postmortem Brains of Alzheimer Patients," Canadian Journal of Physiology and Pharmacology, 1989, vol. 67 (1), pp. 75-78.

McLeod R.L., et al., "Combined Histamine H1 and H3 Receptor Blockade Produces Nasal Decongestion in an Experimental Model of Nasal Congestion," American Journal of Rhinology, 1999, vol. 13 (5), pp. 391-399.

McLeod R.L., et al., "Histamine $H_3$ Antagonists," Progress in Respiratory Research, 2001, vol. 31, pp. 133-136.

Medhurst A.D., et al., "Structually Novel Histamine H3 Receptor Antagonists GSK207040 and GSK334429 Improve Scopolamine-induced Memory Impairment and Capsaicin-Induced Secondary Allodynia in Rats," Biochemical Pharmacology, 2007, vol. 73, pp. 1182-1194.

(56) References Cited

OTHER PUBLICATIONS

Medhurst S.J., et al., "Novel histamine H3 receptor antagonists GSK189254 and GSK334429 are efficacious in surgically-induced and virally-induced rat models of neuropathic pain," Pain, 2008, vol. 138 (1), pp. 61-69.

Meguro K., et al., "Effects of Thioperamide, a Histamine H3 Antagonist, on the Step-Through Passive Avoidance Response and Histidine Decarboxylase Activity in Senescence-Accelerated Mice," Pharmacology, Biochemistry and Behavior, 1995, vol. 50 (3), pp. 321-325.

Monti J., et al., "Sleep and Waking During Acute Histamine H.sub.3 Agonist BP2.94 or H.sub.3 Antagonist Carboperamide (MR 16155) Administration in Rats," Neuropsychopharmacology, 1996, vol. 15 (1), pp. 31-35.

Monti J.M., et al., "Effects of Selective Activation or Blockade of the Histamine H.Sub.3 Receptor on Sleep and Wakefulness," Journal of Pharmacology, 1991, vol. 205, pp. 283-287.

Morisset S., et al., "Atypical Neuroleptics Enhance Histamine Turnoer in Brain Via 5-Hydroxytryptamino.sub.2A Receptor Blockade," Journal of Pharmacology and Experimental Therapeutics, 1999, vol. 288 (2), pp. 590-596.

Murakami K., et al., "AQ-0145, A Newly Developed Histamine H.sub.3 Antagonist, Decreased Seizure Susceptibility of Electrically Induced Convulsions In Mice," Methods and Findings in Experimental and Clinical Pharmacology, 1995, vol. 17 Suppl C, pp. 70-73.

O'Neill A.B., et al., "Pharmacological Evaluation of the In Vivo Model of Vestibular Dysfunction in the Rat," Methods and Findings in Experimental and Clinical Pharmacology, 1999, vol. 21 (4), pp. 285-289.

Onodera K., et al., "Improvement by FUB 181, A Novel Histamine H 3-Receptor Antagonist, of Learning and Memory in the Elevated Plus-Maze Test in Mice," Naunyn-Schmiedebergs' Archives of Pharmacology, 1998, vol. 357 (5), pp. 508-513.

Onodera K., et al., "Neuropharmacology of the Histaminergic Neuron System in the Brain and its Relationship with Behavioral Disorders," Progress in Neurobiology, 1994, vol. 42 (6), pp. 685-702.

Pan J.B., et al., "Histaminergic Ligands Attenuate Barrel Rotation in Rats Following Unilateral Labyrinthectomy," Methods and Findings in Experimental and Clinical Pharmacology , 1998, vol. 20 (9), pp. 771-777.

Panula P., et al., "Neuronal Histamine Deficit in Alzheimer's Disease," Neuroscience, 1998, vol. 82 (4), pp. 993-997.

Passani M.B., et al., "Central Histaminergic System and Cognition," Neuroscience and Biobehavioral Reviews, 2000, vol. 24 (1), pp. 107-113.

Perez-Garcia C., et al., "Effects of Histamine H.sub.3 Receptor Ligands in Experimental Models of Anxiety and Depression," Psychopharmacology, 1999, vol. 142 (2), pp. 215-220.

Prast H., et al., "Histaminergic Neurons Facilitate Social Memory in Rats," Brain Research, 1996, vol. 734 (1-2), pp. 316-318.

Prescott D.M., "Methods in Cell Biology", Academic Press, 1976, Table of Contents.

Pu Y.M., et al., "A Facile and Scaleable Synthesis of ABT-239, A Benzofuranoid H3 Antagonist," Organic Process Research and Development, 2005, vol. 9, pp. 45-50.

Rodrigues A.A., et al., "Interaction of Clozapine with the Histamine H3 Receptor in Rat Brain," British Journal of Pharmacology, 1995, vol. 114 (8), pp. 1523-1524.

Sakai N., et al., "Effects of Thioperamide, A Histamine H3 Receptor Antagonist, On Locomotor Activity and Brain Histamine Content in Mast Cell-Deficient Wiwv Mice," Life Sciences, 1991, vol. 48 (25), pp. 2397-2404.

Sakata T., et al., "Hypothalamic Neuronal Histamine Modulates Ad Libitum Feeding by Rats," Brain research, 1990, vol. 537 (1-2), pp. 303-306.

Sanchez-Lemus E., et al., "Histamine H.Sub.3 Receptor Activation Inhibits Dopamine D.Sub.1 Receptor-Induced Camp Accumulation In Rat Striatal Slices," Neuroscience Letters, 2004, vol. 364 (3), pp. 179-184.

Schwartz J., et al., "Histamine", in: Psychopharmacology: The Fourth Generation of Progress, Chapter 35, Bloom F.E., et al., eds., Raven Press, 1995, pp. 397-405.

Schweitzer J.B., et al., "Drugs Under Investigation for Attention-Deficit Hyperactivity Disorder," Current Opinion in Investigational Drugs, 2002, vol. 3 (8), pp. 1207-1211.

Shaywitz B.A., et al., "Dopaminergic But Not Noradrenergic Mediation of Hyperactivity and Performance Deficits in the Developing Rat Pup," Psychopharmcology, 1984, vol. 82 (1-2), pp. 73-77.

Southam E., et al., "Preclinical Investigations Into the Antipsychotic Potential of the Novel Histamine H.Sub.3 Receptor Antagonist Gsk207040," Psychopharmacology, 2009, vol. 201 (4), pp. 483-494.

Szelag A., "Role of Histamine H.Sub.3-Receptors in the Proliferation Neoplastic Cells in Vitro," Medical Science Monitor, 1998, vol. 4 (5), pp. 747-755.

Tedford C.E., "Pharmacological Characterization of Gt-2016, A Non-Thiourea-Containing Histamine H.Sub.3 Antagonist: in Vitro and in Vivo Studies," The Journal of Pharcamology and Experimenal Therapeutics, 1995, vol. 275 (2), pp. 598-604.

Tedford et al., "Cognition and Locomotor Activity in the Developing Rat: Comparisons of Histamine H.sub.3 Receptor Antagonists and ADHD Therapeutics," Society for Neurosceince Abstr, vol. 22, pp. 22, 1996.

Tietje K.R., et al., "Preclinical Characterization of A-582941: A Novel alpha7 Neuronal Nicotinic Receptor Agonist with Broad Spectrum Cognition-Enhancing Properties," CNS Neuroscience and Therapeutics, 2008, vol. 14 (1), pp. 65-82.

Tozer M., et al., "Histamine H3 Receptor Antagonist," Expert Opinion Therapeutic Patents, 2000, vol. 10 (7), pp. 1045-1055.

Vogel H.G., ed., Drug Discovery and Evaluation: Pharmacological Assays, 2nd Edition, Springer-Verlag Berlin Heidelberg, 2002, pp. 702-706.

Vohora D., et al., "Thioperamide, A Selective Histamine H.sub.3 Receptor Antagonist, Protects Against PTZ-Induced Seizures in Mice," Life Sciences, 2000, vol. 66 (22), pp. PL297-PL301.

Wada H., et al., "Is the Histaminergic Neuron System a Regulatory Center for Whole-Brain Activity", Trends in Neurosciences, 1991, vol. 14 (9), pp. 415-418.

Yates, S.L., et al., "Effects of a novel histamine H3 receptor antagonist, GT2394, on food intake and weight gain in Sprague-Dawley rats," Society for Neuroscience, vol. 102 (10), pp. 219, 2000.

Yates S.L., et al., "Identification and Pharmacological Characterization of a Series of New 1H-4-Substituted-Imidazoyl Histamine H3 Receptor Ligands," Journal of Pharmacology and Experimental Therapeutics, 1999, vol. 289 (2), pp. 1151-1159.

Yawata I., et al., "Role of Histaminergic Neurons in Development of Epileptic Seizures in EI Mice," Brain Research. Molecular Brain Research, 2004, vol. 132 (1), pp. 13-17.

Yokoyama H., et al., "Clobenpropit (Vuf-9153), a New Histamine H3 Receptor Antagonist, Inhibits Electrically Induced Convulsions in Mice," European Journal of Pharmacology, 1994, vol. 260 (1), pp. 23-28.

Yokoyama H., et al., "Effect of Thioperamide, a Histamine H3 Receptor Antagonist, on Electrically Induced Convulsions in Mice," Journal of Pharmacology, 1993, vol. 234 (1), pp. 129-133.

Yokoyama H., et al., "Histamine and Seizures Implications for the Treatment of Epilepsy," CNS Drugs, 1996, vol. 5 (5), pp. 321-330.

MERCAPTOAMIDINE DERIVATIVES AND METHODS OF USE

CROSS-REFERENCE TO RELATED APPLICATION

This claims priority to U.S. Provisional Patent Application No. 61/522,656, filed on Aug. 11, 2011, the contents of which are herein fully incorporated by reference.

BACKGROUND OF THE INVENTION

1. Technical Field

The invention relates to mercaptoamidine derivatives, compositions comprising such compounds, methods for making the compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Arrang J M, et al. Nature 1983, 302: 832-837), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists (Arrang J M, et al. Nature 1987, 327: 117-123; Leurs R and Timmerman H eds. "The Histamine $H_3$ Receptor: a Target for New Drugs," Elsevier (1998)).

The activity at the $H_3$ receptors can be modified or regulated by the administration of $H_3$ receptor ligands. The ligands can demonstrate antagonist, inverse agonist, agonist, or partial agonist activity. $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

The invention is directed to mercaptoamidines and, more particularly, tricyclic mercaptoamidine derivatives having a structure of formula (I):

or a pharmaceutically acceptable salt, ester, amide, or radiolabelled form thereof, wherein:

$R^1$ is hydrogen or $C_1$-$C_4$-alkyl;

$R^2$, at each occurrence, is independently hydrogen or $C_1$-$C_4$-alkyl;

$R^3$, at each occurrence, is independently hydrogen or methyl;

$R^4$, at each occurrence, is independently hydrogen, alkyl, alkenyl, alkynyl, cyano, cyanoalkyl, halogen, haloalkyl, —$OR^x$, —$OC(O)R^x$, —$OC(O)N(R^x)(R^y)$, —$SR^y$, —$S(O)R^w$, —$S(O)_2R^w$, —$S(O)_2N(R^x)(R^y)$, —$C(O)R^w$, —$C(O)OR^y$, —$C(O)N(R^x)(R^y)$, —$N(R^x)(R^y)$, —$N(R^x)C(O)R^w$, —$N(R^x)C(O)O(R^y)$, or —$N(R^x)S(O)_2(R^w)$;

$R^v$, $R^w$, $R^x$, and $R^y$, at each occurrence, are independently hydrogen, alkyl, or haloalkyl;

$L^1$ is O or S;

$G^1$ is phenyl or monocyclic heteroaryl, wherein $G^1$ is unsubstituted or substituted with 1, 2, 3, or 4 substituents selected from $C_1$-$C_4$-alkyl, $C_1$-$C_4$-fluoroalkyl or fluoro;

$G^2$ is selected from (i) or (ii), wherein, $R^5$, $R^6$, $R^7$ and $R^8$ are, at each occurrence, independently selected from the group consisting of hydrogen, alkyl, cycloalkyl, fluoroalkyl, and hydroxyalkyl;

$R^9$ and $R^{10}$ are, at each occurrence, independently selected from the group consisting of hydrogen, alkyl, alkoxy, alkylamino, dialkylamino, fluoro, hydroxy, and hydroxyalkyl;

$R^{11}$, $R^{12}$, $R^{13}$ and $R^{14}$ are, at each occurrence, independently selected from the group consisting of hydrogen, alkyl, fluoroalkyl, and hydroxyalkyl;

Q is selected from the group consisting of a bond, O, S, and $NR^{15}$; wherein $R^{15}$ is hydrogen, alkyl, —$C(O)R^w$, or —$C(O)N(R^x)(R^y)$;

m is 2, 3, 4, 5 or 6;

n is 1, 2, 3, 4, or 5; and p is 0 and q is 0; or p is 1 and q is 1; or p is 1 and q is 0.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating, or preventing conditions and disorders related to $H_3$ receptor modulation in mammals. More particularly, the method is useful for treating or preventing conditions and disorders related to memory and cognition processes, neurological processes, cardiovascular function, pain, and body weight. Accordingly, the compounds and compositions of the invention are useful as a medicament for treating or preventing H₃ receptor modulated disease.

The compounds, compositions comprising the compounds, methods for making the compounds, and methods for treating or preventing conditions and disorders by administering the compounds are further described herein.

DETAILED DESCRIPTION OF THE INVENTION

Compounds of formula (I) are disclosed in this invention

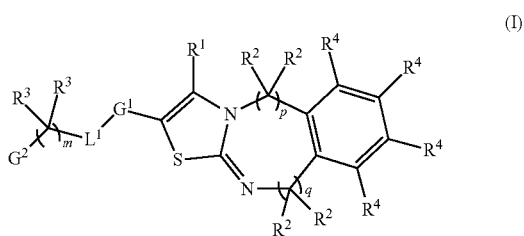

(I)

wherein $G^1$, $G^2$, $L^1$, $R^1$, $R^2$, $R^3$, $R^4$, m, p and q are as defined above in the Summary of the Invention. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds which can be isolated from a reaction mixture.

Definition of Terms

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double bond. Representative examples of alkenylene include, but are not limited to, —CH=CH— and —CH₂CH=CH—.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" means an alkyl group appended to the parent molecular moiety through an amino group, as defined herein. Representative examples of alkylamino include, but are not limited to, methylamino, ethylamino, and sec-butylamino The term "alkylene" denotes a divalent group derived from a straight or branched chain hydrocarbon containing from 1 to 10 carbon atoms. Representative examples of alkylene include, but are not limited to, —CH₂—, —CH₂CH₂—, —CH₂CH₂CH₂—, —CH₂CH₂CH₂CH₂—, and —CH₂CH(CH₃)CH₂—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein means an —NH₂ group.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane(octahydro-2,5-methanopentalene or noradamantane), and tricyclo[3.3.1.1$^{3,7}$]decane(adamantane). The monocyclic, bicyclic, and tricyclic cycloalkyls can be unsubstituted or substituted, and are attached to the parent molecular moiety through any substitutable atom contained within the ring system.

The term "dialkylamino," as used herein, refers to two independent alkyl groups, as defined herein, appended to the parent molecular moiety through an amino group, as defined herein. Representative examples of dialkylamino include, but are not limited to, dimethylamino, diethylamino, ethylmethylamino, butylmethylamino, ethylhexylamino, and the like.

The term "fluoroalkyl" as used herein, means an alkyl group, as defined herein, in which one, two, three, four, five or six hydrogen atoms are replaced by fluorine. Representative examples of haloalkyl include, but are not limited to, fluoromethyl, 2-fluoroethyl, 2,2,2-trifluoroethyl, trifluoromethyl, difluoromethyl, pentafluoroethyl, and trifluoropropyl such as 3,3,3-trifluoropropyl.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo [2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo [3.3.1.1$^{3,7}$]decane), and oxa-adamantane (2-oxatricyclo [3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

As used herein, the term "antagonist" encompasses and describes compounds that prevent receptor activation by an $H_3$ receptor agonist alone, such as histamine, and also encompasses compounds known as "inverse agonists". Inverse agonists are compounds that not only prevent receptor activation by an $H_3$ receptor agonist, such as histamine, but also inhibit intrinsic $H_3$ receptor activity.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{125}I$.

Compounds of the Invention

Compounds of the invention can have the formula (I) as described in the Summary of the Invention.

Particular values of variable groups in compounds of formula (I) are as follows. Such values can be used where appropriate with any of the other values, definitions, claims or embodiments defined hereinbefore or hereinafter.

In one embodiment, $R^1$ is hydrogen or $C_1$-$C_4$-alkyl.
In another embodiment, $R^1$ is hydrogen.
In another embodiment, $R^1$ is $C_1$-$C_4$-alkyl.
In a further embodiment, $R^1$ is methyl.
In one embodiment, $R^2$, at each occurrence, is independently hydrogen or $C_1$-$C_4$-alkyl.
In another embodiment, $R^2$, at each occurrence is $C_1$-$C_4$-alkyl.
In a further embodiment, $R^2$, at each occurrence is hydrogen.
In one embodiment, $R^3$, at each occurrence, is independently hydrogen or methyl.
In another embodiment, $R^3$, at each occurrence, is methyl.
In another embodiment, $R^3$, at one occurrence is methyl, and at all other occurrences is hydrogen.
In a further embodiment, $R^3$, at each occurrence, is hydrogen.
In one embodiment, $R^4$, at each occurrence, is independently hydrogen, alkyl, alkenyl, alkynyl, cyano, cyanoalkyl, halogen, haloalkyl, —$OR^x$, —$OC(O)R^x$, —$OC(O)N(R^x)(R^y)$, —$SR^y$, —$(O)R^w$, —$S(O)_2R^w$, —$S(O)_2N(R^x)(R^y)$, —$C(O)R^w$, —$C(O)OR^y$, —$C(O)N(R^x)(R^y)$, —$N(R^x)(R^y)$, —$N(R^x)C(O)R^w$, —$N(R^x)C(O)O(R^y)$, or —$N(R^x)S(O)_2(R^w)$; wherein, $R^y$, $R^w$, $R^x$, and $R^y$, at each occurrence, are independently hydrogen, alkyl, or haloalkyl.
In a further embodiment, $R^4$, at each occurrence, is hydrogen.
In one embodiment, $L^1$ is O or S.
In another embodiment, $L^1$ is S.
In a further embodiment, $L^1$ is O.

In one embodiment, $G^1$ is phenyl or monocyclic heteroaryl, wherein $G^1$ is unsubstituted or substituted with 1, 2, 3 or 4 substituents selected from $C_1$-$C_4$-alkyl, $C_1$-$C_4$-fluoroalkyl or fluoro.

In another embodiment, $G^1$ is phenyl, wherein $G^1$ is unsubstituted or substituted with 1, 2, 3 or 4 substituents selected from $C_1$-$C_4$-alkyl, $C_1$-$C_4$-fluoroalkyl or fluoro.

In another embodiment, $G^1$ is monocyclic heteroaryl, wherein $G^1$ is unsubstituted or substituted with 1, 2, 3 or 4 substituents selected from $C_1$-$C_4$-alkyl, $C_1$-$C_4$-fluoroalkyl or fluoro.

In another embodiment $G^1$ is (iii); wherein 1 of $X^5$, $X^6$, $X^7$, $X^8$ and $X^9$ is —$C$-$L^1$-$[C(R^3)_2]_m$-$G^2$; 0, 1, or 2 of $X^5$, $X^6$, $X^7$, $X^8$ and $X^9$ are N and the others of $X^5$, $X^6$, $X^7$, $X^8$ and $X^9$ are $CR^{16}$; wherein $R^{16}$, at each occurrence, is independently hydrogen, $C_1$-$C_4$-alkyl, $C_1$-$C_4$-fluoroalkyl or fluoro; and $L^1$, $R^3$, $G^2$, and m are as defined in the Summary of the Invention.

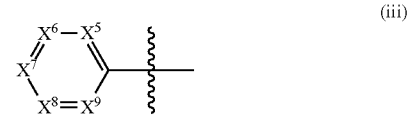

(iii)

In another embodiment, $G^1$ is (iv); wherein $X^5$, $X^6$, $X^8$ and $X^9$ are each $CR^{16}$; and $R^{16}$, at each occurrence, is independently hydrogen, $C_1$-$C_4$-alkyl, $C_1$-$C_4$-fluoroalkyl or fluoro.

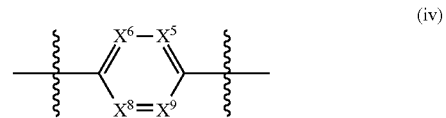

(iv)

In another embodiment, $G^1$ is selected form the group consisting of

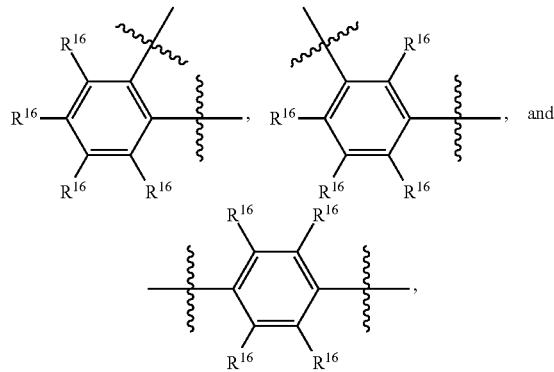

wherein, $R^{16}$, at each occurrence is hydrogen, $C_1$-$C_4$-alkyl, $C_1$-$C_4$-fluoroalkyl or fluoro.

In another embodiment, $G^1$ is

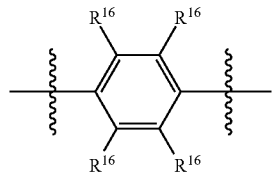

wherein, $R^{16}$, at each occurrence is hydrogen, $C_1$-$C_4$-alkyl, $C_1$-$C_4$-fluoroalkyl or fluoro.

In another embodiment, $G^1$ is

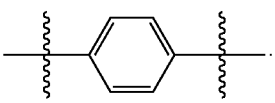

In a further embodiment, $G^1$ is selected from the group consisting of

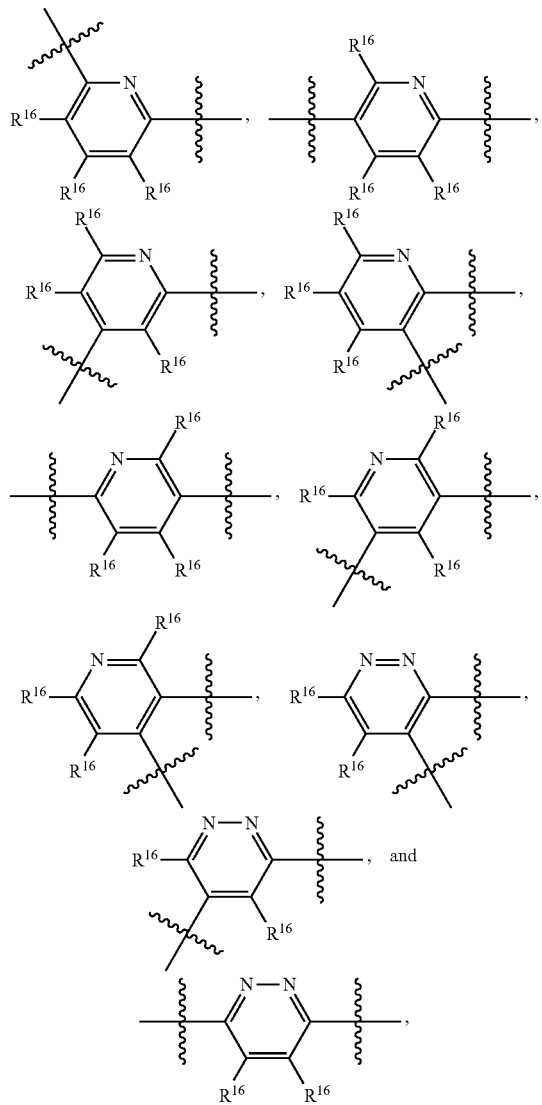

wherein, $R^{16}$, at each occurrence is hydrogen, $C_1$-$C_4$-alkyl, $C_1$-$C_4$-fluoroalkyl or fluoro.

In one embodiment, $G^2$ is selected from (i) or (ii), (i)

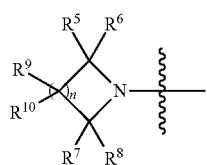

(ii)

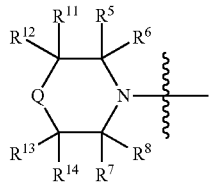

wherein, $R^5$, $R^6$, $R^7$ and $R^8$ are, at each occurrence, independently selected from the group consisting of hydrogen, alkyl, cycloalkyl, fluoroalkyl, and hydroxyalkyl; $R^9$ and $R^{10}$ are, at each occurrence, independently selected from the group consisting of hydrogen, alkyl, alkoxy, alkylamino, dialkylamino, fluoro, hydroxy, and hydroxyalkyl; $R^{11}$, $R^{12}$, $R^{13}$ and $R^{14}$ are, at each occurrence, independently selected from the group consisting of hydrogen, alkyl, fluoroalkyl, and hydroxyalkyl; Q is selected from the group consisting of a bond, O, S, and $NR^{15}$; wherein $R^{15}$ is hydrogen, alkyl, —C(O)$R^w$, or —C(O)N($R^x$)($R^y$); $R^w$, $R^x$, and $R^y$ are independently hydrogen, alkyl, or haloalkyl; and n is 1, 2, 3, 4, or 5.

In another embodiment, $G^2$ is selected from

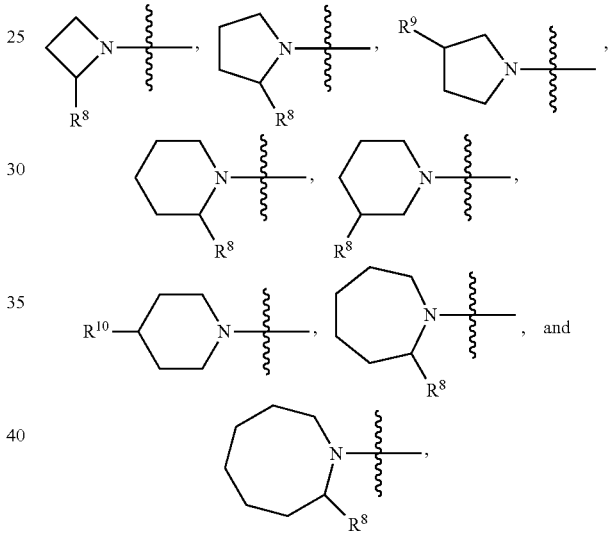

wherein, $R^8$ is hydrogen, alkyl, or hydroxyalkyl; and $R^9$ and $R^{10}$ are alkyl, alkoxy, alkylamino, dialkylamino, fluoro, hydroxy, or hydroxyalkyl.

In a further embodiment, $G^2$ is selected from

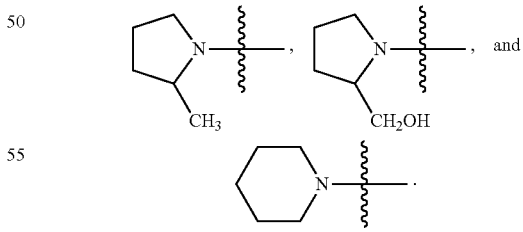

In another embodiment, $G^2$ is selected from

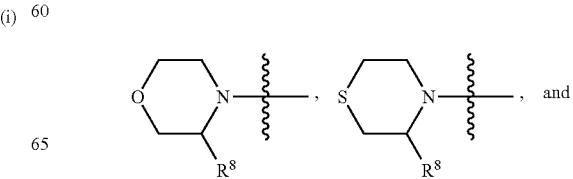

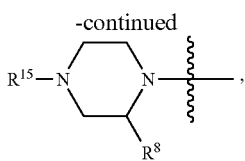

wherein, $R^8$ is hydrogen, alkyl, or hydroxyalkyl; $R^{15}$ is hydrogen, alkyl, —C(O)$R^w$, or —C(O)N($R^x$)($R^y$); and $R^w$, $R^x$, and $R^y$ are independently hydrogen, alkyl, or haloalkyl.

In a further embodiment, $G^2$ is

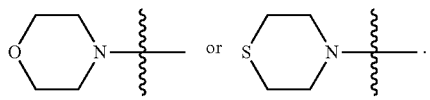

In one embodiment, a compound of formula (I) is selected from

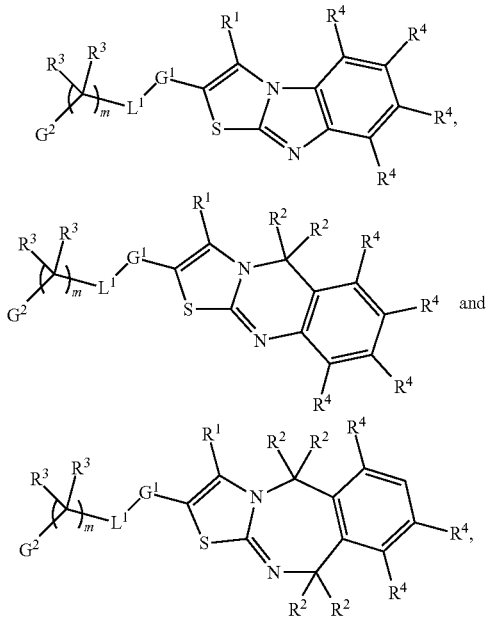

wherein, $R^1$, $R^2$, $R^3$, $R^4$, $G^1$, $G^2$, $L^1$ and m are as defined above.

In another embodiment, a compound of formula (I) is

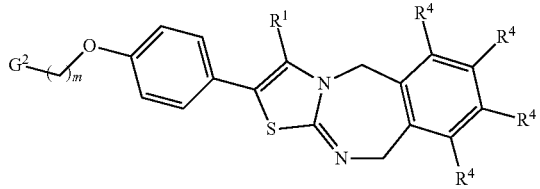

wherein, $R^1$, $R^4$, $G^2$, and m are as defined above.

In a further embodiment, a compound of formula (I) is

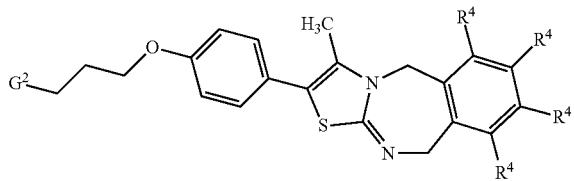

wherein, $R^4$ is as defined above and $G^2$ is selected from

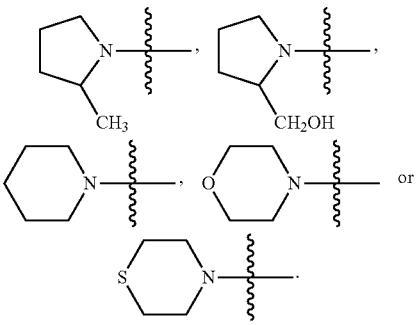

Specific embodiments contemplated as part of the invention also include, but are not limited to, compounds of formula (I), as defined, for example:

((2S)-1-{3-[4-(3-methyl-5,10-dihydro [1,3]thiazolo[3,2-b][2,4]benzodiazepin-2-yl)phenoxy]propyl}pyrrolidin-2-yl)methanol;

3-methyl-2-[4-(3-piperidin-1-ylpropoxy)phenyl]-5,10-dihydro[1,3]thiazolo[3,2-b][2,4]benzodiazepine;

3-methyl-2-(4-{3-[(2R)-2-methylpyrrolidin-1-yl]propoxy}phenyl)-5,10-dihydro[1,3]thiazolo[3,2-b][2,4]benzodiazepine; and 3-methyl-2-[4-(3-morpholin-4-ylpropoxy)phenyl]-5,10-dihydro[1,3]thiazolo[3,2-b][2,4]benzodiazepine.

Compound names are assigned by using Struct=Name naming algorithm as part of CHEMDRAW® ULTRA v. 9.0.7.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present invention also includes isotopically-labeled compounds, which are identical to those recited in Formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

Methods for Preparing Compounds of the Invention

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-2.

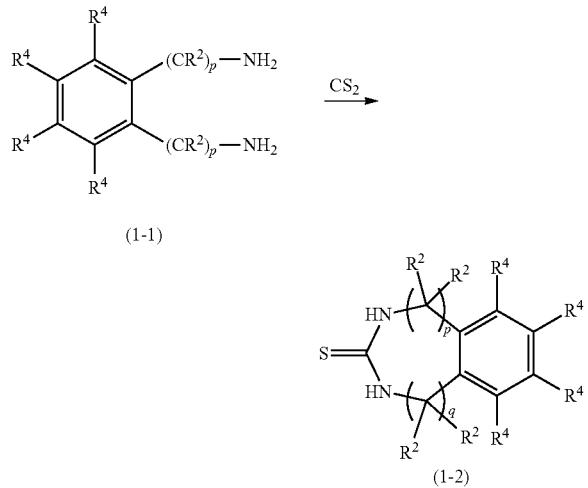

Compounds of formula (1-2), wherein $R^2$, $R^4$, p and q are as defined in the Summary of the Invention can be prepared as illustrated in Scheme 1. Compounds of formula (1-1) can be reacted with carbon disulfide in a solvent such as ethanol at or near ambient temperature to give an intermediate dithiocarbamic acid which can be isolated. This intermediate can be cyclized with heating in a solvent such as 2-methoxyethanol to give compounds of formula (1-2) (Elslager E F, et al. Journal of Heterocyclic Chemistry 1968; 5: 609-613).

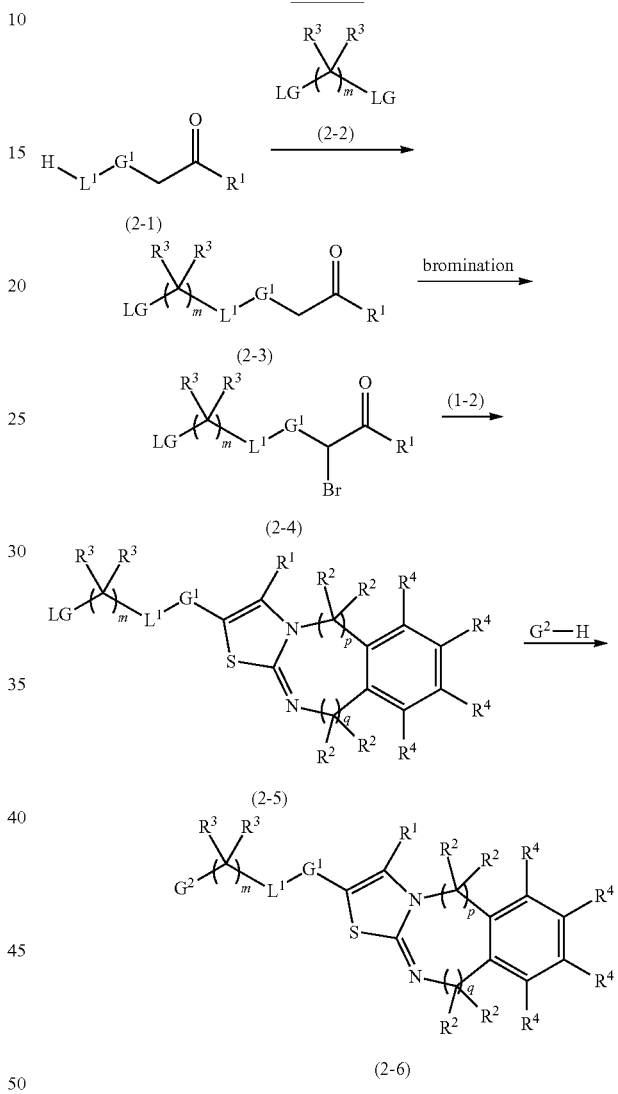

Compounds of formula (2-6), wherein $G^1$, $G^2$, $L^1$, $R^1$, $R^2$, $R^3$, $R^4$, m, p and q are as defined in the Summary of the Invention can be prepared as illustrated in Scheme 2. Compounds of formula (2-1), wherein $L^1$ is O or S, can be alkylated with compounds of formula (2-2), wherein LG is a suitable leaving group such as a halogen other than fluorine or a sulfonate to give compounds of formula (2-3). The alkylation can be performed in the presence of a base such as but not limited to potassium carbonate or cesium carbonate. The reaction can be performed in an optionally heated solvent such as 2-butanone. Compounds of formula (2-3) can be brominated to give compounds of formula (2-4). The bromination can be accomplished with reagents such as but not limited to (2-carboxyethyl)triphenylphosphonium tribromide, bromine, or pyridine hydrobromide perbromide in such solvents as tetrahydrofuran, carbon tetrachloride, methylene chloride, dioxane, diethyl ether, benzene, and acetic acid. Compounds of formula (2-4) can be reacted with compounds of formula (1-2) from Scheme 1 to give compounds of formula (2-5). The transformation can be carried out in heated 2-methoxyethanol or ethylene glycol. Compounds of formula (2-5) can be reacted with heterocycles of formula $G^2$-H, wherein the hydrogen resides on nitrogen atom of the heterocycle, $G^2$, to give compounds of formula (2-6). The reaction can be carried out in a solvent such as optionally heated acetonitrile in the presence of an optional base such as potassium carbonate or cesium carbonate. Compounds of formula (2-6) are representative of compounds of formula (I).

There are many suitable and readily available heterocycles of formula $G^2$-H, wherein $G^2$ is as defined in formula (I).

TABLE 1

Examples of readily available amines of formula $G^2$-H.

| Amines | Structures | Commercial Source, Chemical Abstracts Number (CAS #), or Literature Reference |
|---|---|---|
| azetidine | 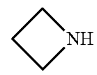 | CAS# 503-29-7, Aldrich |
| pyrrolidine | 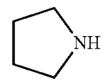 | CAS# 123-75-1, Aldrich |
| (R)-2-methylpyrrolidine L-tartrate | 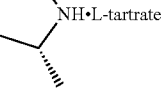 | International Publication No. WO 2004043458; Pu Y, et al. Organic Process Research & Development 2005; 9: 45-50 |
| (S)-2-methylpyrrolidine L-tartrate | 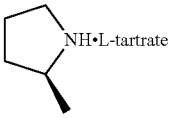 | Kim M-J, et al. Bioorg. Med. Chem. Lett. 1996; 6(1): 71-76. Gaffield W, et al. Tetrahedron 1981; 37: 1861-1869. |
| L-prolinol | 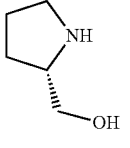 | CAS# 23356-96-9, Aldrich |
| (S)-2-fluoromethylpyrrolidine | 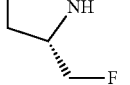 | CAS # 460748-85-0, prepared according to the procedure described in: International Publication No. WO 2004043458 |
| piperidine | 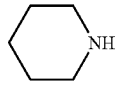 | CAS# 110-89-4, Aldrich |
| 2-methylpiperidine | 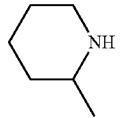 | CAS# 109-05-7, Aldrich |
| (R)-2-methylpiperidine | 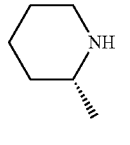 | Clariant Life Science Molecules Sandycroft Deeside Clwyd CH5 2PX UNITED KINGDOM |
| 4-fluoropiperidine hydrochloride | 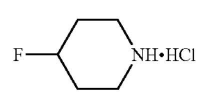 | ABCR GmbH & CO. KG P.O. Box 21 01 35 76151 Karlsruhe GERMANY |
| (R)-3-hydroxypiperidine hydrochloride | 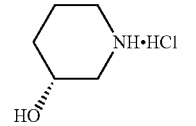 | CAS# 198976-43-1, Aldrich |

TABLE 1-continued

Examples of readily available amines of formula $G^2$-H.

| Amines | Structures | Commercial Source, Chemical Abstracts Number (CAS #), or Literature Reference |
| --- | --- | --- |
| morpholine | O-CH2CH2-NH (six-membered ring) | CAS# 110-91-8, Aldrich |
| hexamethyleneimine | seven-membered ring with NH | CAS# 100-97-0, Aldrich |

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, Greene's Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts or esters, or amides derived from inorganic or organic acids. The term "pharmaceutically acceptable salts and esters and amides", as used herein, refer to carboxylate salts, amino acid addition salts, zwitterions, and esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$-alkyl esters and $C_5$-to-$C_7$-cycloalkyl esters, although $C_1$-to-$C_4$-alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$-alkyl amines and secondary $C_1$-to-$C_6$-dialkyl amines. In the case of secondary amines, the amine may also be in the form of a 5- or 6-membered heterocycle containing one nitrogen atom. Amides derived from ammonia, $C_1$-to-$C_3$-alkyl primary amides and $C_1$-to-$C_2$-dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of histamine-3 receptors in cells, the compounds described in the invention can affect physiological processes in humans and animals. In this way, the compounds and compositions described in the invention are useful for treating and preventing diseases and disorders modulated by histamine-3 receptors. Typically, treatment or prevention of such diseases and disorders can be effected by selectively modulating the histamine-3 receptors in a mammal, by administering a compound or composition of the invention, either alone or in combination with another active agent as part of a therapeutic regimen.

The compounds of the invention, including but not limited to those specified in the examples, possess an affinity for the histamine-3 receptors and therefore, the compounds of the invention may be useful for the treatment and prevention of diseases or conditions such as attention-deficit hyperactivity disorder (ADHD), deficits in attention, dementia, and diseases with deficits of memory, learning, schizophrenia, cognitive deficits of schizophrenia, cognitive deficits and dysfunction in psychiatric disorders, Alzheimer's disease, mild cognitive impairment, epilepsy, seizures, allergic rhinitis, and asthma, motion sickness, dizziness, Meniere's disease, vestibular disorders, vertigo, obesity, diabetes, type II diabetes, Syndrome X, insulin resistance syndrome, metabolic syndrome, pain, including neuropathic pain, osteoarthritis pain, neuropathy, sleep disorders, narcolepsy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome. The ability of histamine-3 receptor modulators, and consequently the compounds of the invention, to prevent or treat such disorders is demonstrated by examples found in the following references.

The ability of the compounds of the invention, including, but not limited to, those specified in the examples, to treat attention-deficit hyperactivity disorder (ADHD), and deficits in attention, may be demonstrated by Cowart M, et al. J. Med. Chem. 2005; 48: 38-55; Fox G B, et al. Journal of Pharmacology and Experimental Therapeutics 2005; 313: 176-190; Fox, G B, et al. Behavioural Brain Research 2002; 131(1,2): 151-161; Yates S L, et al. Journal of Pharmacology and Experimental Therapeutics 1999; 289: 1151-1159; Ligneau X, et al. Journal of Pharmacology and Experimental Therapeutics 1998; 287: 658-666; Tozer M, Expert Opinion Therapeutic Patents 2000; 10: 1045; Halpern M T, 1999; 1: 524-527; Shaywitz B A, et al. Psychopharmacology 1984; 82:73-77; Dumery V, et al. Exp. Brain Res. 1987; 67: 61-69; Tedford C E, et al. J. Pharmacol. Exp. Ther. 1995; 275:598-604; Tedford C E, et al. Soc. Neurosci. Abstr., 1996; 22:22; and Fox G B et al. Behav. Brain Res. 2002; 131:151-161; Glase S A, et al. Annual Reports in Medicinal Chemistry 2002; 37: 11-20; Schweitzer J B, et al. Current Opinion in Investigative Drugs 2002; 3: 1207.

The ability of the compounds of the invention, including, but not limited to, those specified in the examples, to treat dementia, and diseases with deficits of memory and learning, may be demonstrated by Fox, G B, et al. Journal of Pharmacology and Experimental Therapeutics 2003; 305(3): 897-908; Fox G B Inflammation Research 2003; 52(Suppl. 1): S31-S32; Bernaerts P, et al. Behavioural Brain Research 2004; 154: 211-219; Onodera K, et al. Nauyn-Schmiedeberg's Arch. Pharmacol. 1998; 357: 508-513; Prast H, et al. Brain Research 1996; 734: 316-318; Chen Z, et al. Brain Research 1999; 839: 186-189; Passani MB, et al. Neuroscience and Biobehavioral Reviews 2000; 24:107-113.

The ability of the compounds of the invention, including, but not limited to, those specified in the examples, to treat schizophrenia, cognitive deficits of schizophrenia, and cognitive deficits, may be demonstrated by Fox G., et al. Journal of Pharmacology and Experimental Therapeutics 2005; 313: 176-190 and by Browman, K E, et al. Behavioural Brain Research 2004; 153: 69-76; Komater V A, et al. Psychopharmacology 2003; 167: 363-372; Rodrigues A A, et al. British Journal of Pharmacology 1995; 114: 1523-1524; Passani M B, et al. Neuroscience and Biobehavioral Reviews 2000; 24: 107-113; Morriset, S., et al. Journal of Pharmacology and Experimental Therapeutics 1999; 288: 590-596; and Southam, E. et al. Psychopharmacology 2009; 201: 483-494.

The ability of the compounds of the invention, including, but not limited to, those specified in the examples, to treat dysfunction in psychiatric disorders, Alzheimer's disease, and mild cognitive impairment may be demonstrated by Meguro K, et al. Pharmacology, Biochemistry and Behavior 1995; 50: 321-325; Esbenshade T, et al. Biochemical Pharmacology 2004; 68: 933-945; Huang, Y.-W., et al. Behavioural Brain Research 2004; 151: 287-293; Mazurkiewicz-Kwilecki I M, et al. Can. J. Physiol. Pharmacol. 1989; 67: 75-78; Panula P, et al. Neuroscience 1997; 82: 993-997; Haas H L, et al. Behav. Brain Res. 1995; 66: 41-44; De Almeida MAMR, et al. Arch. Int. Pharmacodyn. 1986; 283: 193-198; Kamei C, et al. Psychopharmacology 1990; 102: 312-318; Kamei C, et al. Jpn. J. Pharmacol. 1991; 57: 437-482; Schwartz et al., Psychopharmacology, The Fourth Generation of Progress. Bloom and Kupfer (eds). Raven Press, New York, (1995) 397; and Wada H, et al., Trends in Neurosci. 1991;14: 415-418.

The ability of the compounds of the invention, including, but not limited to, those specified in the examples, to treat epilepsy, and seizures, may be demonstrated by Harada C., et al. Brain Research Bulletin 2004; 63: 143-146; as well as by Yokoyama H, et al., Eur. J. Pharmacol. 1993; 234: 129-133; Yokoyama H, et al. European Journal of Pharmacology 1994; 260: 23; Yokoyama H, et al. CNS Drugs 1996; 5: 321; Vohora D, Life Sciences 2000; 66: PL297-PL301; Onodera K, et al., Prog. Neurobiol. 1994; 42: 685; Chen, Z., et al. British Journal of Pharmacology 2004; 143: 573-580; Leurs R, et al. Progress in Drug Research 1995; 45: 170-165; Leurs R, et al. Prog. Drug Res. 1992; 39: 127; Yokoyama H. et al. CNS Drugs 1995; 5: 321-330; and Hurukami K, et al. Meth. Find. Exp. Clin. Pharmacol. 1995;17(C): 70-73; Yawata I, et al. Molecular Brain Research 2004; 132: 13-17; and Schwartz J-C, et al. International Publication No. WO 2006/103537 A2.

The ability of the compounds of the invention, including, but not limited to, those specified in the examples, to treat allergic rhinitis, and asthma, may be demonstrated by McLeod R L, et al. Am. J. Rhinol 1999a; 13; 391-399; McLeod R L, et al. Progress in Respiratory Research 2001; 31 (in New Drugs for Asthma, Allergy and COPD): 133-136; Delaunois A, et al. European Journal of Pharmacology 1995; 277: 243-250; Dimitriadou V, et al. Clinical Science 1994; 87: 151-163.

The ability of the compounds of the invention, including, but not limited to, those specified in the examples, to treat motion sickness, dizziness, Meniere's disease, vestibular disorders, and vertigo, may be demonstrated by Pan J B, et al. Methods and Findings in Clinical Pharmacology 1998; 20: 771-777; O'Neill A B, et al. Methods and Findings in Clinical Pharmacology 1999; 21: 285-289; and by Leurs R, et al. Progress in Drug Research 1995; 45: 170-165, Lozada A F, et al. BioMedCentral Neuroscience 2004; 5:32.

The ability of the compounds of the invention, including, but not limited to, those specified in the examples, to treat obesity, diabetes, type II diabetes, Syndrome X, insulin resistance syndrome, and metabolic syndrome, may be demonstrated by Hancock, A A European Journal of Pharmacology 2004; 487: 183-197; Hancock A A, et al. Inflamm. Res. 200; 53 Supplement 1: S47-S48; as well as by Itoh E, et al. Biol. Psych. 1999; 45: 475-481; Yates S I, et al. Abstracts, Society for Neuroscience 2000; 102.10: 219; and Bjenning C, et al., Abstracts, International Sendai Histamine Symposium, Sendai, Japan, #P39 (November, 2000); Sakata T, et al. Brain Research 1990; 537: 303-306.

The ability of the compounds of the invention, including, but not limited to, those specified in the examples, to treat pain, including neuropathic pain and neuropathy, has been demonstrated by diverse research labs, including Malmberg-Aiello P, et al. British Journal of Pharmacology 1994; 111: 1269-1279; Hriscu A, et al. Farmacia 2001; 49: 23-30, 76. Recently, additional demonstrations of the efficacy of H3 antagonists in neuropathic pain have appeared, including Medhurst A D, et al. Biochemical Pharmacology 2007; 73: 1182-1194; and Medhurst S J, et al. Pain 2008; 138: 61-69.

The ability of the compounds of the invention, including, but not limited to, those specified in the examples, to treat sleep disorders, including narcolepsy and pathological sleepiness, and jet lag, may be demonstrated by Barbier A J, et al. British Journal of Pharmacology 2004; 1-13; Monti J M, et al. Neuropsychopharmacology 1996; 15: 31-35; Lin J S, et al. Brain Res. 1990; 523: 325-330; Ligneau X, et al. Journal of Pharmacology and Experimental Therapeutics 1998; 287: 658-666; Sakai N, et al. Life Sci. 1991; 48: 2397-2404; Mazurkiewicz-Kwilecki I M, et al. Can. J. Physiol. Pharmacol. 1989; 67: 75-78; Panula P, et al. Neuroscience 1998; 44: 465-481; Wada H, et al. Trends in Neuroscience 1991; 14: 415; and Monti J M, et al. Eur. J. Pharmacol. 1991; 205: 283; Dvorak C., et al. Journal of Medicinal Chemistry 2005; 48: 2229-2238; and Schwartz, J-C, et al. International Publication No. WO 2006/103546 A2.

Amphetamine is an abused stimulant in humans. It, and similar abused drugs stimulate locomotor activity in animals, and it has been found that the $H_3$ antagonist thioperamide suppresses the locomotor stimulation induced by amphetamine; therefore $H_3$ antagonists are likely to be useful for treating drug abuse as may be demonstrated by Clapham J., et al. European Journal of Pharmacology 1994; 259: 107-14.

The ability of the compounds of the invention, including, but not limited to, those specified in the examples, to treat mood alteration, bipolar disorder, depression, obsessive compulsive disorder, and Tourette's syndrome, may be demonstrated by Lamberti C, et al. British Journal of Pharmacology 1998; 123: 1331-1336; Perez-Garcia C, et. al. Psychopharmacology (Berlin) 1999; 142: 215-20.

The ability of the compounds of the invention, including, but not limited to, those specified in the examples, to treat Parkinson's disease (a disease wherein patients have deficits in ability to initiate movements, and patients' brain have low dopamine levels) may be demonstrated by Sanchez-Lemus E, et al. Neuroscience Letters 2004; 364: 179-184; Sakai N, et al., Life Sci. 1991; 48: 2397-2404; Fox, G B, et al. Journal of Pharmacology and Experimental Therapeutics 2005; 313: 176-190; Chen Z., et al. British Journal of Pharmacology 2004; 143: 573-580; and Schwartz, J-C, et al. International Publication No. WO 2006/103546 A2.

The ability of the compounds of the invention, including, but not limited to, those specified in the examples, to treat medullary thyroid carcinoma, melanoma, polycystic ovary syndrome, may be demonstrated by Szelag A, Med. Sci. Monitor 1998; 4: 747-755; and Fitzsimons C H, et al. Inflammation Res. 1998; 47 (Suppl 1): S50-S51.

Compounds of the invention are particularly useful for treating and preventing a condition or disorder affecting memory or cognition, for example Alzheimer's disease, attention-deficit hyperactivity disorder, schizophrenia, the cognitive deficits of schizophrenia, or pain.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 30 mg/kg/day. For purposes of oral administration, more preferable doses can be in the range of from about 0.0003 to about 1 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

EXAMPLES

Abbreviations: APCI for atmospheric pressure chemical ionization; aq for aqueous; HPLC for high-performance liquid chromatography; and psi for pounds per square inch.
Description of High Throughput Purification Method Using Trifluoroacetic acid (HTP-TFA Method).

Samples were purified by preparative HPLC on a Phenomenex® Luna® C8(2) 5 μm 100 Å AXIA™ column (30 mm×75 mm) A gradient of acetonitrile (A) and 0.1% trifluoroacetic acid in water (B) was used, at a flow rate of 50 mL/minute (0-0 5 minutes 10% A, 0.5-7.0 minutes linear gradient 10-95% A, 7.0-10.0 minutes 95% A, 10.0-12.0 minutes linear gradient 95-10% A). Samples were injected in 1.5 mL dimethyl sulfoxide:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson® 506C interface box; and two Gilson® FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan® LCQ using 70:30 methanol:10 mM NH$_4$OH(aq) at a flow rate of 0.8 mL/minute. Loop-injection mass spectra were acquired using a Finnigan® LCQ running LCQ Navigator 1.2 software and a Gilson® 215 liquid handler for fraction injection controlled by an Abbott developed Visual Basic application.

Example 1

((2S)-1-{3-[4-(3-methyl-5,10-dihydro[1,3]thiazolo[3,2-b][2,4]benzodiazepin-2-yl)phenoxy]propyl}pyrrolidin-2-yl)methanol Example 1A 1,2-phenylenedimethanamine Phthalazine (21.5 g, 0.165 mol), 10% palladium on carbon (2 g), and methanol (125 mL) were combined in a pressure bottle and shaken at room temperature under 60 psi of hydrogen for 5 days. Raney-nickel® slurry (6.42 g) and 10% palladium on carbon (0.50 g) were added, and the mixture was shaken at 50° C. under 60 psi of hydrogen for 16 hours. The mixture was filtered through a nylon membrane and concentrated to give the titled compound: $^1$H NMR (300 MHz, DMSO-d$_6$) δ ppm 7.32 (dd, J=5.4, 3.5 Hz, 2H), 7.17 (dd, J=5.6, 3.4 Hz, 2H), 3.74 (s, 4H); MS (DCI/NH$_3$) m/z 137 (M+H)$^+$.

Example 1B 4,5-dihydro-1H-benzo[e][1,3]diazepine-3(2H)-thione

A solution of the product from Example 1A (10.7 g, 79 mmol) in ethanol (120 mL) was added dropwise to a solution of carbon disulfide (9.4 mL, 160 mmol) in ethanol (80 mL), and the mixture was stirred overnight at room temperature. The precipitate was collected by filtration, washed with ethanol and dried. The solid was suspended in 2-methoxyethanol (50 mL), and the mixture was heated to 130° C. for 2 hours before being allowed to cool to room temperature overnight. The solid was collected by filtration, washed with diethyl ether and dried under vacuum to provide the title compound: $^1$H NMR (300 MHz, DMSO-d$_6$) δ ppm 8.12 (t, J=3.6, 2H), 7.34-7.21 (m, 4H), 4.36 (d, J=4.8, 4H); MS (DCI/NH$_3$) m/z 179 (M+H)$^+$.

Example 1C 1-(4-(3-bromopropoxy)phenyl)propan-2-one

A mixture of 1-(4-hydroxyphenyl)propan-2-one (1 g, 6.67 mmol), 1,3-dibromopropane (0.74 mL, 7.3 mmol) and potassium carbonate (1.84 g, 13 3 mmol) in 2-butanone (30 mL) was heated to reflux for 16 hours. The reaction mixture was cooled to ambient temperature and partitioned between ethyl acetate and water. The organic phase was separated, and the aqueous phase was extracted with additional ethyl acetate. The organic extracts were combined, washed with brine, dried (MgSO$_4$), filtered and concentrated under reduced pressure. The residue obtained was chromatographed on silica gel eluting with 10% ethyl acetate/hexanes to provide the title compound: $^1$H NMR (300 MHz, CDCl$_3$) δ ppm 2.14 (s, 3H), 2.36-2.27 (m, 2H), 3.60 (t, J=6.4 Hz, 2H), 3.63 (s, 2H), 4.09 (t, J=5.8 Hz, 2H), 6.87 (d, J=8.7 Hz, 2H), 7.11 (d, J=8.7 Hz, 2H); MS (DCI/NH$_3$) m/z 288 (M+NH$_4$)$^+$.

Example 1D 1-bromo-1-(4-(3-bromopropoxy)phenyl)propan-2-one

To a solution of the product from Example 1C (865 mg, 3.19 mmol) in anhydrous tetrahydrofuran (30 mL) was slowly added a tetrahydrofuran (10 mL) solution of (2-carboxyethyl)triphenylphosphonium tribromide (1.85 g, 3.19 mmol) at 0° C. The mixture was then stirred at ambient temperature for 2 hours. The mixture was partitioned between ethyl acetate and water. The layers were separated, and the aqueous layer was washed with additional ethyl acetate. The organic fractions were combined, washed with brine, dried (MgSO$_4$), filtered, and concentrated. The residue was chromatographed on silica gel eluting with 10% ethyl acetate/hexanes to provide the title compound: $^1$H NMR (300 MHz, CDCl$_3$) δ ppm 2.31 (s, 3H), 2.37-2.27 (m, 2H), 3.60 (t, J=6.4 Hz, 2H), 4.11 (t, J=5.8 Hz, 2H), 5.42 (s, 1H), 6.90 (d, J=8.8 Hz, 2H), 7.36 (d, J=8.8 Hz, 2H); MS (DCI/NH$_3$) m/z 366 (M+NH$_4$)$^+$.

Example 1E (E)-2-(4-(3-bromopropoxy)phenyl)-3-methyl-5,10-dihydrobenzo[e]thiazolo[3,2-a][1,3]diazepine A solution of the product from Example 1B (325 mg, 0.93 mmol) and the product from Example 1D (157 mg, 0.88 mmol) in 2-methoxyethanol (30 mL) was heated to 60° C. for 30 minutes. The temperature was raised to 130° C., and the reaction mixture was stirred for 3 hours. The mixture was cooled to ambient temperature and diluted with ether. An oily solid was triturated with ether and dried under vacuum to provide the title compound. $^1$H NMR (300 MHz, DMSO-d$_6$) δ ppm 2.30-2.21 (m, 2H), 2.39 (s, 3H), 3.67 (t, J=6.5 Hz, 2H), 4.13 (t, J=6.0 Hz, 2H), 4.93 (s, 2H), 5.54 (s, 2H), 7.07 (d, J=8.8 Hz, 2H), 7.35 (d, J=8.7 Hz, 2H), 7.52-7.44 (m, 3H), 7.66 (dd, J=4.8, 3.1 Hz, 1H); MS (DCI/NH$_3$) m/z 429 (M+H)$^+$.

Example 1F ((2S)-1-{3-[4-(3-methyl-5,10-dihydro[1,3]thiazolo[3,2-b][2,4]benzodiazepin-2-yl)phenoxy]propyl}pyrrolidin-2-yl)methanol A mixture of the product from Example 1E (228 mg, 0 5 mmol), L-prolinol (51 mg, 0.6 mmol), potassium carbonate (345 mg, 2.5 mmol) and acetonitrile (1.3 mL) was heated to 50° C. overnight. The mixture was diluted with dichloromethane, filtered, concentrated and purified by HPLC (HTP-TFA method) and rechromatographed on silica gel eluting with a gradient of 5%, 7.5% and 10% (9:1 methanol: ammonium hydroxide) in dichloromethane to provide the title compound: $^1$H NMR (300 MHz, CDCl$_3$) δ ppm 1.83-2.28 (m, 8H) 2.34 (s, 3H) 2.93-3.06 (m, 1H) 3.14-3.29 (m, 1H) 3.80-3.94 (m, 4H) 4.01-4.13 (m, 2H) 4.92 (s, 2H) 5.29 (s, 2H) 6.88 (d, J=8.81 Hz, 2H) 7.15 (d, J=8.48 Hz, 2H) 7.32 - 7.37 (m, 1H) 7.39-7.53 (m, 3H); MS (DCI/NH$_3$) m/z 450 (M+H)$^+$.

Example 2

3-methyl-2-[4-(3-piperidin-1-ylpropoxy)phenyl]-5,10-dihydro[1,3]thiazolo[3,2-b][2,4]benzodiazepine The title compound was prepared using the procedure described in Example 1F substituting piperidine for L-prolinol: $^1$H NMR (300 MHz, CDCl$_3$) δ ppm 1.54-1.70 (m, 3H) 1.79-1.93 (m, 7H) 2.14-2.26 (m, 2H) 2.92-3.04 (m, 4H) 3.07-3.14 (m, 1H) 4.06 (t, J=5.76 Hz, 2H) 4.94 (s, 2H) 5.25 (s, 2H) 6.88 (d, J=8.48 Hz, 2H) 7.16 (d, J=8.81 Hz, 2H) 7.29-7.35 (m, 1H) 7.38-7.52 (m, 3H); MS (DCI/NH$_3$) m/z 434 (M+H)$^+$.

Example 3

3-methyl-2-(4-{3-[(2R)-2-methylpyrrolidin-1-yl]propoxy}phenyl)-5,10-dihydro[1,3]thiazolo[3,2-b][2,4]benzodiazepine The title compound was prepared using the procedure described in Example 1F substituting (R)-2-methylpyrrolidine for L-prolinol: $^1$H NMR (300 MHz, CDCl$_3$) δ ppm 1.56 (d, J=6.78 Hz, 3H) 1.89-2.31 (m, 4H) 2.35 (s, 3H) 2.43-2.70 (m, 2H) 2.80-3.63 (m, 4H) 3.96-4.15 (m, 3H) 4.93 (s, 2H) 5.28 (s, 2H) 6.90 (d, J=8.81 Hz, 2H) 7.18 (d, J=8.81 Hz, 2H) 7.32-7.36 (m, 1H) 7.41-7.53 (m, 3H); MS (DCI/NH$_3$) m/z 434 (M+H)$^+$.

Example 4

3-methyl-2-[4-(3-morpholin-4-ylpropoxy)phenyl]-5,10-dihydro[1,3]thiazolo[3,2-b][2,4]benzodiazepine The title compound was prepared using the procedure described in Example 1F substituting morpholine for L-prolinol: $^1$H NMR (300 MHz, CDCl$_3$) δ ppm 2.24-2.38 (m, 2H) 2.34 (s, 3H) 2.87-3.01 (m, 2H) 3.25-3.33 (m, 2H) 3.60-3.68 (m, 2H) 3.91-4.05 (m, 4H) 4.09 (t, J=5.59 Hz, 2H) 4.91 (s, 2H) 5.29 (s, 2H) 6.88 (d, J=8.81 Hz, 2H) 7.16 (d, J=8.48 Hz, 2H) 7.31-7.38 (m, 1H) 7.41-7.54 (m, 3H); MS (DCI/NH$_3$) m/z 436 (M+H)$^+$.

Determination of Biological Activity

To determine the effectiveness of representative compounds of this invention as histamine-3 receptor ligands (H$_3$ receptor ligands), the following tests were conducted according to previously described methods (see Arrang J M, et al. European Journal of Pharmacology 1990; 188: 219-227; Tedford C E, et al. Journal of Pharmacology and Experimental Therapeutics 1995; 275: 598-604; Leurs R, et al. Journal of Pharmacology and Experimental Therapeutics 1996; 276: 1009-1015; and Cheng Y-C, et al. Biochemical Pharmacology 1973; 22: 3099-3108).

Membranes expressing native H$_3$ receptors from rat cerebral cortices were prepared by homogenization in cold TE buffer containing protease inhibitors as described previously (Esbenshade T A, et al. Biochemical Pharmacology 2004; 68: 933-945). The homogenate was centrifuged at 40,000 g for 20 minutes at 4° C., the pellet resuspended by homogenization, centrifuged as in the previous step and the resulting pellet resuspended in TE buffer in 6.25 volumes (wet weight/volume). Aliquots were frozen at −70° C. until needed.

Membrane preparations were incubated with [$^3$H]-N-α-methylhistamine (0.5-1.0 nM) in the presence or absence of increasing concentrations of ligands for H$_3$ receptor competition binding. The binding incubations were conducted in a final volume of 0.5 mL TE buffer at 25° C. and were terminated after 30 minutes. Thioperamide (30 µM) was used to define non-specific binding. All binding reactions were terminated by filtration under vacuum onto polyethylenimine (0.3%) presoaked Unifilters (Perkin Elmer Life Sciences) or Whatman GF/B filters followed by three brief washes with 2 mL of ice-cold TE buffer. Bound radiolabel was determined by liquid scintillation counting. For all of the radioligand competition binding assays, $IC_{50}$ values and Hill slopes were determined by Hill transformation of the data and $pK_i$ values were determined by the Cheng-Prusoff equation. The general method for determining potency in competition binding assays is also suitable for determining the potency of compounds at the human $H_3$ receptor, as specifically described in Esbenshade T A, et al. Journal of Pharmacology and Experimental Therapeutics 2005; 313: 165-175.

Generally, representative compounds of the invention demonstrated binding affinities at the histamine $H_3$ receptor range from about 0.02 nM to about 1000 nM. Preferred compounds of the invention bound to histamine-3 receptors with binding affinities from about 0.02 nM to about 100 nM. More preferred compounds of the invention bound to histamine-3 receptors with binding affinities from about 0.02 nM to about 1 nM. Binding activity of Examples are indicated in Table 2.

TABLE 2

Binding Activity

| Example | rat cortex (pKi) | rat cortex (Ki, nM) |
|---|---|---|
| 1 | 10.5 | 0.032 |
| 2 | 10.3 | 0.050 |
| 3 | 10.7 | 0.020 |
| 4 | 9.49 | 0.324 |

Compounds of the invention are histamine-3 receptor ligands that modulate function of the histamine-3 receptor by altering the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor or they may be agonists that activate the receptor.

In addition to the utility of in vitro methods for characterizing the potency of compounds at the $H_3$ receptor, there are animal disease models available which can demonstrate the utility of compounds. There are a number of methods to test the activity of compounds in different pain models that are well known to those skilled in the art. Pain states are exhibited by humans and other animals, and there are numerous animal models of pain; a review of animal models of pain is found in Joshi S K, et al. Expert Opinion in Drug Discovery 2006; 1: 323-334. A description of the formalin test in rats, neuropathic pain models in rats, general descriptions of methods of testing and descriptions of pain models are found in the book 'Drug Discovery and Evaluation, $2^{nd}$ edition' (H. Gerhard Vogel, editor; Springer-Verlag, N.Y., 2002; pp. 702-706).

Determination of Analgesic Effect Against Neuropathic Pain

Animals are prepared for testing, by use of a surgical procedure that induces neuropathic pain in one paw. Male Sprague Dawley rats are purchased from Charles River (Portage, Mich.). Prior to surgery, animals are housed in groups and maintained in a temperature-regulated environment. Following nerve ligation surgery, animals are housed in groups, and have access to food and water ad libitum.

The L5 and L6 spinal nerves of anesthetized rats are tightly ligated in a manner described previously (see Kim S H, et al. Pain 1992; 50: 355-363). An incision is made on the dorsal portion of the hip and the muscle is blunt-dissected to reveal the spinal processes. The L6 transverse process is removed, and the left side L5 and L6 spinal nerves are tightly ligated with 5.0 braided silk suture. The wound is cleaned, the membrane is sewn with 4.0 dissolvable Vicryl suture and the skin is closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation is evaluated using testing with von Frey filaments. As described previously by Chaplan R S, et al. J. Neurosci. Meth. 1994; 53: 55-63, two weeks following surgery rats are acclimated to a testing box constructed of plexiglass with a wire mesh floor which allowed access to the plantar surface of the animal's hindpaws. Using an Up-Down method (Dixon W J, Annual Rev. Pharmacol. Toxicol. 1980; 20: 441-462; Chaplan R S, et al. J. Neurosci. Meth. 1994; 53: 55-63), von Frey filaments of increasing stiffness are applied to the plantar surface of the hindpaws and the withdrawal response of the animals is observed; for the surgically affected paw with neuropathic pain (the left side paw) the baseline level of allodynia has a withdrawal threshold of 4 g of pressure. By comparison, for the control paw without allodynia (in this case the right side paw), the typical withdrawal pressure is around 15 g. The efficacy of the compound in reducing neuropathic pain at different doses is determined by comparing response in the surgery-affected paw versus the response in the control paw. This is expressed as the MPE (maximum percent effect), or 100 times the withdrawal threshold of the allodynic (left side) divided by the withdrawal threshold of the control (right side).

Activity in an Osteoarthritis Model

Unilateral knee joint osteoarthritis is induced in rats by a single intra-articular (i.a.) injection of sodium monoiodoacetate (MIA) (Sigma-Aldrich, St. Louis, Mo.) (3 mg in 50 µL sterile isotonic saline) into the right knee joint cavity under light (1-3%) isoflurane anesthesia.

Pain behavior is assessed by measurement of hind limb grip force (GF) in adult osteoarthritic rats. Following the unilateral injection of MIA (male Sprague Dawley, 325-350 g, tested at 20 days following MIA injection), a behavioral measure of activity-induced pain is carried out. Measurements of the peak hind limb grip force are conducted by recording the maximum compressive force (CF.), in grams of force, exerted on a hind limb strain gauge setup, in a commercially available grip force measurement system (Columbus Instruments, Columbus, Ohio).

During testing, each rat is gently restrained by grasping it around its rib cage and then allowed to grasp the wire mesh frame attached to the strain gauge. The experimenter then moved the animal in a rostral-to-caudal direction until the grip is broken. Each rat is sequentially tested twice at approximately 2-3 minute intervals to obtain a raw mean grip force ($CF_{max}$). This raw mean grip force data is in turn converted to a maximum hindlimb cumulative compressive force ($CF_{max}$), as the grams of force/kg of body weight, for each animal.

For evaluating the compound effects, the hind limb grip force is conducted 20 days following the intra-articular injection of MIA. A group of age-matched naive (not injected with MIA) animals is added as a comparator to the drug-dosed groups. The vehicle control response for each group of MIA-treated animals is defined as the 0% response (0% effect), whereas the naive control group is defined as the normal response and as 100% effect. The % effects for each dose group is expressed as % return of response to normalcy, compared to the naive group. That is, the % effect=(Treatment $CF_{max}$–Vehicle $CF_{max}$)/Vehicle $CF_{max}$]×100). All experiments evaluating drug effects in this model are conducted in a randomized blinded fashion.

The ability of compounds to treat diseases with deficits in memory and cognition such as Alzheimer's disease, dementia, age-related cognitive impairment, schizophrenia, and cognitive deficits of schizophrenia can be assessed in animal models. One model assessing the capability of a compound to enhance memory is the single trial 24-hour inhibitory avoidance model, described in Tietje et al. (Tietje K R, et al. CNS Neuroscience and Therapeutics 2008; 14: 65-82).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:
1. A compound of formula (I):

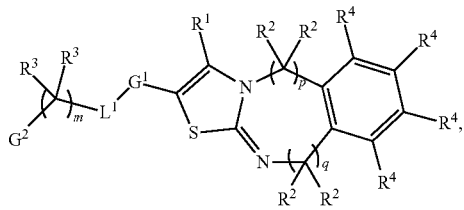

or a pharmaceutically acceptable salt, ester, amide, or radiolabelled form thereof, wherein:
$R^1$ is hydrogen or $C_1$-$C_4$-alkyl;
$R^2$, at each occurrence, is independently hydrogen or $C_1$-$C_4$-alkyl;
$R^3$, at each occurrence, is independently hydrogen or methyl;
$R^4$, at each occurrence, is independently hydrogen, alkyl, alkenyl, alkynyl, cyano, cyanoalkyl, halogen, haloalkyl, —$OR^x$, —$OC(O)R^x$, —$OC(O)N(R^x)(R^y)$, —$SR^y$, —$S(O)R^w$, —$S(O)_2R^w$, —$S(O)_2N(R^x)(R^y)$, —$C(O)R^w$, —$C(O)OR^y$, —$C(O)N(R^x)(R^y)$, —$N(R^x)(R^y)$, —$N(R^x)C(O)R^w$, —$N(R^x)C(O)O(R^y)$, or —$N(R^x)S(O)_2(R^w)$;
$R^v$, $R^w$, $R^x$, and $R^y$, at each occurrence, are independently hydrogen, alkyl, or haloalkyl;
$L^1$ is O or S;
$G^1$ is phenyl or monocyclic heteroaryl, wherein $G^1$ is unsubstituted or substituted with 1, 2, 3, or 4 substituents selected from $C_1$-$C_4$-alkyl, $C_1$-$C_4$-fluoroalkyl or fluoro;
$G^2$ is selected from (i) or (ii),

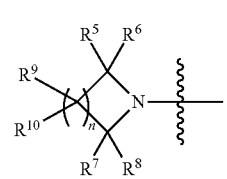

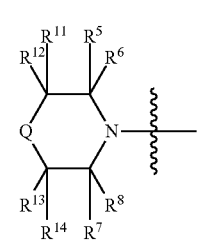

wherein, $R^5$, $R^6$, $R^7$ and $R^8$ are, at each occurrence, independently selected from the group consisting of hydrogen, alkyl, cycloalkyl, fluoroalkyl, and hydroxyalkyl;
$R^9$ and $R^{10}$ are, at each occurrence, independently selected from the group consisting of hydrogen, alkyl, alkoxy, alkylamino, dialkylamino, fluoro, hydroxy, and hydroxyalkyl;
$R^{11}$, $R^{12}$, $R^{13}$ and $R^{14}$ are, at each occurrence, independently selected from the group consisting of hydrogen, alkyl, fluoroalkyl, and hydroxyalkyl;
Q is selected from the group consisting of a bond, O, S, and $NR^{15}$; wherein
$R^{15}$ is hydrogen, alkyl, —C(O) $R^w$, or —$C(O)N(R^x)(R^y)$;
m is 2, 3, 4, 5 or 6;
n is 1, 2, 3, 4, or 5; and
p is 1 and q is 1.
2. The compound of claim 1, wherein $G^1$ is (iii);

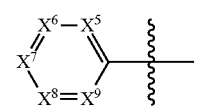

wherein 1 of $X^5$, $X^6$, $X^7$, $X^8$ and $X^9$ is C-$L^1$-$[C(R^3)_2]_m$-$G^2$; 0, 1, or 2 of $X^5$, $X^6$, $X^7$, $X^8$ and $X^9$ are N and the others of $X^5$, $X^6$, $X^7$, $X^8$ and $X^9$ are $CR^{16}$; and
$R^{16}$, at each occurrence, is independently hydrogen, $C_1$-$C_4$-alkyl, $C_1$-$C_4$-fluoroalkyl or fluoro.
3. The compound of claim 1, wherein $G^1$ is (iv);

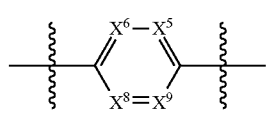

$X^5$, $X^6$, $X^8$ and $X^9$ are N or $CR^{16}$; wherein 0, 1, or 2 of $X^5$, $X^6$, $X^8$ and $X^9$ are N and the others of $X^5$, $X^6$, $X^8$ and $X^9$ are $CR^{16}$; and $R^{16}$, at each occurrence, is independently hydrogen, $C_1$-$C_4$-alkyl, $C_1$-$C_4$-fluoroalkyl or fluoro.

4. The compound of claim 3, wherein
$L^1$ is O;
$R^3$, at each occurrence, is hydrogen;
$G^2$ is (i); and

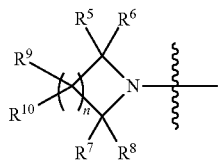

m is 2, 3 or 4.

5. The compound of claim 3, wherein
$L^1$ is O;
$R^3$, at each occurrence, is hydrogen;
$G_2$ is (ii); and

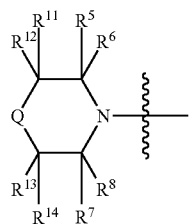

m is 2, 3 or 4.

6. The compound of claim 1, wherein
p is 1;
q is 1; and
$R^2$ at each occurrence is hydrogen; and
$R^4$ is hydrogen.

7. The compound of claim 6, wherein
$R^1$ is $C_1$-$C_4$-alkyl;
$R^3$, at each occurrence, is hydrogen;
$L^1$ is O;
$G^1$ is (iv);

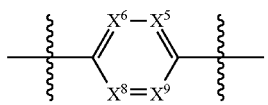

$X^5$, $X^6$, $X^8$ and $X^9$ are each $CR^{16}$;
$R^{16}$, at each occurrence, is independently hydrogen, $C_1$-$C_4$-alkyl, $C_1$-$C_4$-fluoroalkyl or fluoro;
$G^2$ is (i);

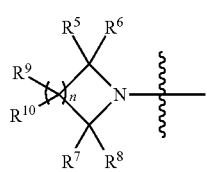

$R^5$ is hydrogen, alkyl, or hydroxyalkyl;
$R^6$, $R^7$, and $R^8$ are each hydrogen;
$R^9$ and $R^{10}$, at each occurrence, are hydrogen;
m is 3; and
n is 1, 2, or 3.

8. The compound of claim 6, wherein
$R^1$ is $C_1$-$C_4$-alkyl;
$R^3$, at each occurrence, is hydrogen;
$L^1$ is O;
$G^1$ is (iv);

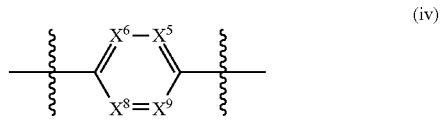

$X^5$, $X^6$, $X^8$ and $X^9$ are each $CR^{16}$;
$R^{16}$, at each occurrence, is independently hydrogen, $C_1$-$C_4$-alkyl, $C_1$-$C_4$-fluoroalkyl or fluoro;
$G^2$ is (ii);

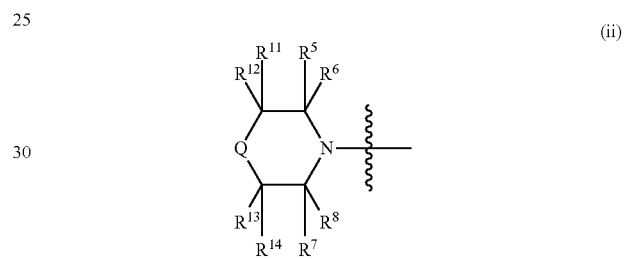

$R^5$ is hydrogen, alkyl, or hydroxyalkyl;
$R^6$, $R^7$, and $R^8$ are each hydrogen;
$R^{11}$, $R^{12}$, $R^{13}$, and $R^{14}$ are each hydrogen;
Q is O or S; and
m is 3.

9. The compound of claim 1, selected from the group consisting of:
((2S)-1-{3-[4-(3-methyl-5,10-dihydro[1,3]thiazolo[3,2-b][2,4]benzodiazepin-2-yl)phenoxy]propyl}pyrrolidin-2-yl)methanol;
3-methyl-2-[4-(3-piperidin-1-ylpropoxy)phenyl]-5,10-dihydro[1,3]thiazolo[3,2-b][2,4]benzodiazepine;
3-methyl-2-(4-{3-[(2R)-2-methylpyrrolidin-1-yl]propoxy}phenyl)-5,10-dihydro[1,3]thiazolo[3,2-b][2,4]benzodiazepine; and
3-methyl-2-[4-(3-morpholin-4-ylpropoxy)phenyl]-5,10-dihydro[1,3]thiazolo[3,2-b][2,4]benzodiazepine.

10. A pharmaceutical composition comprising a therapeutically effective amount of a compound of claim 1 in combination with a pharmaceutically acceptable carrier.

11. A method of treating a condition or disorder selected from the group consisting of neuropathic pain, and osteoarthritis pain, the method comprising administering to a mammal an effective amount of a compound of claim 1.

* * * * *